(12) United States Patent
Campiche et al.

(10) Patent No.: US 9,060,945 B2
(45) Date of Patent: Jun. 23, 2015

(54) USE OF DANIELONE AND DERIVATIVES THEREOF IN SKIN CARE

(71) Applicant: DSM IP Assets B.V., Heerlen (NL)

(72) Inventors: Remo Campiche, Basel (CH); Piero Geotti-Bianchini, Basel (CH); Hugo Ziegler, Basel (CH); Stefan Martin Stoeckli, Basel (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 14/369,850

(22) PCT Filed: Dec. 28, 2012

(86) PCT No.: PCT/EP2012/077014
§ 371 (c)(1),
(2) Date: Jun. 30, 2014

(87) PCT Pub. No.: WO2013/104526
PCT Pub. Date: Jul. 18, 2013

(65) Prior Publication Data
US 2015/0004108 A1 Jan. 1, 2015

(30) Foreign Application Priority Data
Jan. 9, 2012 (EP) ..................... 12150422

(51) Int. Cl.
*A61K 8/35* (2006.01)
*A61Q 19/02* (2006.01)
*A61K 8/97* (2006.01)
*A61Q 17/04* (2006.01)

(52) U.S. Cl.
CPC . *A61K 8/35* (2013.01); *A61Q 19/02* (2013.01); *A61K 8/97* (2013.01); *A61K 2800/10* (2013.01); *A61Q 17/04* (2013.01)

(58) Field of Classification Search
None
See application file for complete search history.

(56) References Cited

U.S. PATENT DOCUMENTS

2013/0203688 A1* 8/2013 Barbeau et al. ................. 514/25

FOREIGN PATENT DOCUMENTS

| JP | 7 206644 | 8/1995 |
| WO | WO 2012/021983 | 2/2012 |

OTHER PUBLICATIONS

NPL Search results (Google); downloaded Feb. 3, 2015.*
U.S. Patent Documents—None.*
International Search Report for PCT/EP2012/077014 mailed Jun. 4, 2013.
F. Echeverri et al., "Danielone, a Phytoalexin from Papaya Fruit", Photochemistry, vol. 44, No. 2, Jan. 1, 1997, pp. 255-256.
S. Nakashima et al., "Melanogenesis Inhibitors from the Desert Plant *Anastatica hierochuntica* in B16 Melanoma Cells", Bioorganic & Medicinal Chemistry, 18(6), pp. 2337-2345.

* cited by examiner

*Primary Examiner* — Jeffrey T Palenik
(74) *Attorney, Agent, or Firm* — Nixon & Vanderhye P.C.

(57) ABSTRACT

The present invention relates to a novel composition comprising danielone and derivatives thereof as well as to the use of such compositions in skin lightening. More particularly, the present invention relates to danielone and derivatives thereof for use in topical compositions for smoothening skin color irregularities, for reducing melanin formation in the human skin, for lightening/brightening human skin and/or for treatment of pigmentation disorders which comprises topically administering an effective amount of danielone and derivatives thereof to the appropriate skin area of a person in need of such beautifying agent, or treatment.

4 Claims, No Drawings

USE OF DANIELONE AND DERIVATIVES THEREOF IN SKIN CARE

This application is the U.S. national phase of International Application No. PCT/EP2012/077014 filed 28 Dec. 2012 which designated the U.S. and claims priority to EP 12150422.9, filed 9 Jan. 2012, the entire contents of each of which are hereby incorporated by reference.

The present invention relates to a novel composition comprising danielone and derivatives thereof as well as to the use of such compositions for skin lightening. More particularly, the present invention relates to danielone and derivatives thereof for use in topical compositions for smoothening skin color irregularities, for reducing melanin formation in the human skin, for lightening/brightening human skin and/or for treatment of pigmentation disorders which comprises topically administering an effective amount of danielone to the appropriate skin area of a person in need of such beautifying agent, or treatment.

There is a growing demand in the industry, and a growing market need for skin lightening products that are stable, safe, and cost efficient. However, the commonly used skin lightening/whitening agents, often lack efficacy, cause stability and safety problems and/or are expensive in use. For example, ascorbic acid may easily be oxidized and is rather unstable in conventional cosmetic products.

Resveratrol (3,4',5 trihydroxystilbene; CAS: 501-36-0) has a structural skeleton comprised of two aromatic rings linked by an ethylene bridge. JP01038009, published in 1989 discloses skin-lightening cosmetics containing hydroxystilbenes. However, resveratrol only exhibits a moderate activity and, due to its low solubility in conventional cosmetic oils, can only be used in low concentrations (<1 wt.-%).

Synthetic skin lighteners such as hydroquinone or kojic acid may cause skin irritation or acute dermatitis.

Ascorbic acid derivatives such as ascorbyl phosphate or ascorbyl-2-glucoside (2-O-α-D-glucopyranosyl-L-Ascorbic acid; CAS: 129499-78-1) only exhibit a moderate in vitro/in vivo efficacy and need to be used in very high concentration levels (>2 wt.-%).

Thus, there is an ongoing need for highly efficient skin lightening products overcoming the drawbacks of the prior art.

Surprisingly, the inventors of the present invention found that danielone and derivatives thereof of formula (1) below strongly inhibit total melanin production and are soluble at high concentration in cosmetic topical compositions, and therefore, can be used in the preparation of topical compositions for cosmetic skin lightening purposes. Said compositions are also useful in pharmaceutical applications for the treatment of pigmentation disorders, and/or for treatment against unwanted pigmentation of human skin.

The term "cosmetics skin lightening" purposes as described above refers to smoothening of skin color irregularities, lightening/brightening of skin, prevention of tanning and/or prevention of re-pigmentation, protection against sun or UV-induced skin darkening and reducing the skin melanin level, enhancement of skin bleaching action and/or action on blemishes.

Therefore, the first object of the present invention is a topical composition comprising a compound of formula (1) formula (1):

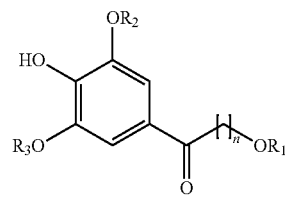

wherein,
n is an integer comprised between 1 and 5,
$R_1$ is H or an aliphatic straight or branched carbon chain of 1 to 5 carbon atoms
$R_2$ and $R_3$ are both independently an aliphatic straight or branched carbon chain of 1 to 6 carbon atoms.

It is essential to obtain a superior whitening activity that both groups $OR_2$ and $OR_3$ are present since when one of the $OR_1$ or $OR_2$ group is replaced by a hydrogen, the whitening activity is drastically reduced.

For all embodiments of the present invention, the compound of formula (1) is preferably a compound wherein n=1, $R_1$ is H or an aliphatic straight or branched carbon chain of 1 to 5 carbon atoms, $R_2$ and $R_3$ are both independently an aliphatic straight or branched carbon chain of 1 to 3 carbon atoms.

More preferably, n=1, $R_1$=H, or an aliphatic straight or branched carbon chain of 1 to 3 carbon atoms, $R_2$ and $R_3$ are both independently an aliphatic straight or branched carbon chain of 1 to 3 carbon atoms. Even more preferably, it is a compound of formula (1) wherein n=1, $R_1$=H, or an aliphatic straight or branched carbon chain of 1 to 3 carbon atoms $R_2$ and $R_3$ are both a methyl group. Most preferred compound according to the present invention is the compound of formula (1), wherein n=1, $R_1$=H, both $R_2$ and $R_3$ are a methyl group, corresponding to 2-hydroxy-1-(4-hydroxy-3,5-dimethoxy-phenyl)-ethanone or danielone (CAS Number: 90426-22-5)

The compounds of formula (1) can be synthesized according to methods known in the art (e.g.: J. G. Luis et al. Chem. Reearc 1999, and F. Echeverri et al. Molecules 2000, 5, 1287-1290). Moreover, danielone can be extracted from papaya fruit as described in Echeverri et al. 1997, Phytochemistry 44, 255-256.

Therefore, it is also an object of the present invention to provide a topical composition comprising a papaya fruit extract, wherein the papaya fruit extract comprises at least 1 wt. % more preferably, at least 10 wt. %, compounds of formula (1), even more preferably, at least 10 wt. % danielone.

Preferably, the topical composition is a cosmetic or a pharmaceutical composition. Most preferably, it is a cosmetic composition.

In another embodiment, the topical composition according the present invention is characterized in that it comprises between 0.0001 and 1 weight-% of a compound of formula (1) based on the total weight of the composition. Preferably, the composition according to the present invention comprises between 0.0001 and 0.5 weight-% of a compound of formula (1) based on the total weight of the composition. More preferably, the composition according to the present invention comprises between 0.0001 and 0.1 weight-% of a compound of formula (1) based on the total weight of the composition.

In another embodiment, the topical composition according to the present invention is characterized in that it comprises at least one additional skin lightening agent and/or UV screening agent, and a conventional carrier. Examples of additional, other skin lightening agents, which may be present in the topical cosmetic or pharmaceutical compositions of the present invention are especially those disclosed in WO 2004/062635, WO 2004/037213, and DE 102 38 449.

A safe and effective amount of a desquamation active may be added to the compositions of the present invention, more preferably from about 0.1% to about 10%, even more preferably from about 0.2% to about 5%, by weight of the composition. Desquamation actives enhance the skin appearance benefits of the present invention. One desquamation system that is suitable for use herein contains sulfhydryl compounds and zwitterionic surfactants and is described in U.S. Pat. No. 5,681,852. Another desquamation system that is suitable for use herein contains salicylic acid and zwitterionic surfactants and is described in U.S. Pat. No. 5,652,228. Zwitterionic surfactants such as described in these applications are also useful as desquamatory agents herein, with cetyl betaine being particularly preferred.

According to the present invention, compounds of formula (1) can be used as such or in an encapsulated form, for example in a liposomal form. Liposomes are preferably formed with lecithins with or without addition of sterols or phytosterols. The encapsulation of the active ingredients can be alone or together with other active ingredients. Other embodiments include solid or semisolid capsules aiming to protect the compound of formula (1) from degradation or for controlled delivery. Suitable encapsulation technologies are for example described in WO 0180823, WO 9903450, WO 9317784 or in Fragrance Journal (2001), 29(2), 83-90.

Additionally the cosmetic and pharmaceutical topical composition of the present invention may contain UV-screening agents. The additional UV-screening agents are advantageously selected from IR, UV-A, UV-B, UV-C and/or broadband filters. Examples of UV-B or broad spectrum screening agents, i.e. substances having absorption maximums between about 290 nm and 340 nm may be organic or inorganic compounds. Organic UV-B or broadband screening agents are e.g. acrylates such as 2-ethylhexyl 2-cyano-3,3-diphenylacrylate (octocrylene, PARSOL® 340), ethyl 2-cyano-3,3-diphenylacrylate and the like; camphor derivatives such as 4-methyl benzylidene camphor (PARSOL® 5000), 3-benzylidene camphor, camphor benzalkonium methosulfate, polyacrylamidomethyl benzylidene camphor, sulfo benzylidene camphor, sulphomethyl benzylidene camphor, therephthalidene dicamphor sulfonic acid and the like; Cinnamate derivatives such as ethylhexyl methoxycinnamate (PARSOL® MCX), ethoxyethyl methoxycinnamate, diethanolamine methoxycinnamate (PARSOL® Hydro), isoamyl methoxycinnamate and the like as well as cinnamic acid derivatives bond to siloxanes; p-aminobenzoic acid derivatives, such as p-aminobenzoic acid, 2-ethylhexyl p-dimethylaminobenzoate, N-oxypropylenated ethyl p-aminobenzoate, glyceryl p-aminobenzoate; benzophenones such as benzophenone-3, benzophenone-4,2,2',4,4'-tetrahydroxy-benzophenone, 2,2'-dihydroxy-4,4'-dimethoxybenzophenone and the like; esters of benzalmalonic acid such as di-(2-ethylhexyl) 4-methoxybenzalmalonate; esters of 2-(4-ethoxy-anilinomethylene)propandioic acid such as 2-(4-ethoxy anilinomethylene) propandioic acid diethyl ester as described in the European Patent Publication EP 0895 776; organosiloxane compounds containing benzmalonate groups as described in the European Patent Publications EP 0358584 B1, EP 0538431 B1 and EP 0709080 A1 such as PARSOL® SLX; drometrizole trisiloxane (Mexoryl XL); imidazole derivatives such as e.g. 2-phenyl benzimidazole sulfonic acid and its salts (PARSOL®HS). Salts of 2-phenyl benzimidazole sulfonic acid are e.g. alkali salts such as sodium- or potassium salts, ammonium salts, morpholine salts, salts of primary, sec. and tert. amines like monoethanolamine salts, diethanolamine salts and the like; salicylate derivatives such as isopropylbenzyl salicylate, benzyl salicylate, butyl salicylate, ethylhexyl salicylate (PARSOL® EHS, Neo Heliopan OS), isooctyl salicylate or homomenthyl salicylate (homosalate, PARSOL® HMS, Neo Heliopan HMS) and the like; triazine derivatives such as ethylhexyl triazone (Uvinul T-150), diethylhexyl butamido triazone (Uvasorb HEB) and the like. Encapsulated UV-filters such as encapsulated ethylhexyl methoxycinnamate (Eusolex UV-pearls) or microcapsules loaded with UV-filters as e.g. disclosed in EP 1471995 and the like;

Examples of broad spectrum or UV A screening agents i.e. substances having absorption maximums between about 320 nm and 400 nm may be organic or inorganic compounds. Organic broad spectrum or UV A screening agents include e.g. dibenzoylmethane derivatives such as 4-tert.-butyl-4'-methoxydibenzoyl-methane (PARSOL® 1789), dimethoxydibenzoylmethane, isopropyldibenzoylmethane and the like; benzotriazole derivatives such as 2,2'-methylene-bis-(6-(2H-benzotriazole-2-yl)-4-(1,1,3,3-tetramethylbutyl)-phenol (Tinosorb M) and the like; bis-ethylhexyloxyphenol methoxyphenyl triazine (Tinosorb S) and the like; phenylene-1,4-bis-benzimidazolsulfonic acids or salts such as 2,2-(1,4-phenylene)bis-(1H-benzimidazol-4,6-disulfonic acid) (Neoheliopan AP); amino substituted hydroxybenzophenones such as 2-(4-Diethylamino-2-hydroxy-benzoyl)-benzoic acid hexylester (Uvinul A plus) as described in the European Patent Publication EP 1046391; Ionic UV-A filters as described in the International Patent Publication WO2005080341 A1; As dibenzoylmethane derivatives have limited photostability it may be desirable to photostabilize these UV-A screening agents. Thus, the term "conventional UV-A screening agent" also refers to dibenzoylmethane derivatives such as e.g. PARSOL® 1789 stabilized by, e.g. 3,3-Diphenylacrylate derivatives as described in the European Patent Publications EP 0 514 491 B1 and EP 0 780 119 A1; Benzylidene camphor derivatives as described in the U.S. Pat. No. 5,605,680; Organosiloxanes containing benzmalonate groups as described in the European Patent Publications EP 0358584 B1, EP 0538431 B1 and EP 0709080 A1.

A good overview of UV-A and UV-B screening agents which can be added to the compositions of the present invention can also be found in DE-A 103 27 432. All UV-filter compounds disclosed in this document are also useful as components for the compositions of the present invention and are included herein by reference.

A safe and effective amount of the UV-screening agent is used, typically from about 1 wt.-% to about 20 wt.-%, more typically from about 2 wt.-% to about 10 wt.-%.

Other suitable UV-screening agents which may be incorporated into the topical cosmetic or pharmaceutical compositions of the present invention are inorganic pigments such as microparticulated metal oxides (e.g. PARSOL® TX). Examples of such compounds include e.g. titanium dioxide having an average primary particle size of from about 15 nm to about 100 nm, zinc oxide having an average primary particle size of from about 15 nm to about 150 nm, zirconium oxide having an average primary particle size of from about 15 nm to about 150 nm, iron oxide having an average primary particle size of from about 15 nm to about 500 nm, and mixtures thereof. The metal oxide particles may also be coated by metal oxides such as e.g. aluminum or zirconium oxides or by organic coatings such as e.g. polyols, methicone, aluminum stearate, alkyl silane. Such coatings are well known in the art. When used herein, the inorganic sunscreens are present in the amount of from about 0.1 wt.-% to about 20 wt.-%, preferably from about 0.5 wt.-% to about 10 wt.-%, more preferably from about 1 wt.-% to about 5 wt.-%.

In another embodiment, the topical composition according to the present invention is characterized in that it is a pharmaceutical composition intended for the application onto human skin.

Conventional carriers comprise excipients or diluents conventionally used in topical compositions. If nothing else is stated, the excipients, additives, diluents, etc. mentioned in the following are suitable for both pharmaceutical and cosmetic compositions. The necessary amounts of the cosmetic and dermatological adjuvants and additives can, based on the desired product, easily be determined by the skilled person.

Regarding the kind of the topical cosmetic and pharmaceutical composition and the preparation of the topical cosmetic and pharmaceutical preparations as well as for further suitable additives, it can be referred to the pertinent literature, e.g. to Novak G. A., Die kosmetischen Präparate—Band 2, Die kosmetischen Präparate—Rezeptur, Rohstoffe, wissenschaftliche Grundlagen (Verlag für Chem. Industrie H. Ziolkowski KG, Augsburg).

Preferably, the topical cosmetic or pharmaceutical compositions of the present invention are in the form of a suspension or dispersion in solvents or fatty substances, or alternatively in the form of an emulsion or micro emulsion (in particular of O/W or W/O type, O/W/O or W/O/W-type), PET-emulsions, multiple emulsions, bickering emulsions, hydrogels, alcoholic gels, lipogels, one or multiphase solutions or a vesicular dispersion and other usual compositions, which can also be applied by pens, as masks or as sprays. The emulsions can also contain anionic, nonionic, cationic or amphoteric surfactant(s).

Preferred topical cosmetic or pharmaceutical compositions according to the invention are skin (face) care preparations, decorative preparations, light protection preparations and functional preparations.

Examples of skin care preparations are, in particular, face creams, body oils, body lotions, body gels, treatment creams, skin protection ointments, shaving preparations, such as shaving foams or gels, moisturizing gels, moisturizing sprays, revitalizing body sprays, cellulite gels, face and/or body moisturizers, facial and/or body cleansers, face masks, anti acne preparations and/or peeling preparations. Most preferred are face care products.

Preferred topical cosmetic or pharmaceutical compositions according to the invention are skin care preparations, or functional preparations.

Examples of decorative preparations are, in particular, lipsticks, eye shadows, mascaras, dry and moist make-up formulations, rouges, powders, and/or suntan lotions.

Examples of functional preparations are cosmetic compositions containing further active ingredients such as hormones, vitamins, vegetable and/or fruit extracts, anti-ageing ingredients, and/or antimicrobial (antibacterial or antifungal) ingredients without being limited thereto.

Cosmetic compositions in accordance with the present invention can be in the form of a liquid, lotion, a thickened lotion, a gel, a cream, a milk, an ointment, a paste, a powder, a make-up, or a solid tube stick and can be optionally be packaged as an aerosol and can be provided in the form of a mousse such as a aerosol mousse, a foam or a spray foams, sprays, sticks, a gel, a plaster, a powder, a cleanser, a soap or aerosols or wipes. Preferred topical compositions comprise a cream, a gel, an ointment, a lotion a tincture, a spray, a mousse, a cleansing composition or foam.

The topical cosmetic or pharmaceutical compositions of the invention can also contain usual cosmetic or pharmaceutical adjuvants and additives, such as preservatives/antioxidants, fatty substances/oils, water, organic solvents, silicones, thickeners, softeners, emulsifiers, sunscreens, antifoaming agents, moisturizers, fragrances, surfactants, fillers, sequestering agents, anionic, cationic, nonionic or amphoteric polymers or mixtures thereof, propellants, acidifying or basifying agents, dyes, colorants, pigments or nanopigments, e.g. those suited for providing a photoprotective effect by physically blocking out ultraviolet radiation, or any other ingredients usually formulated into topical cosmetic or pharmaceutical compositions. The necessary amounts of the cosmetic and dermatological adjuvants and additives can, based on the desired product, easily be chosen by a skilled artisan in this field and will be illustrated in the examples, without being limited hereto. The usual cosmetic adjuvants and additives such as emulsifiers, thickeners, surface active ingredients and film formers can show synergistic which can be determined by the expert in the field with normal trials, or with the usual considerations regarding the formulation of topical cosmetic or pharmaceutical composition.

An additional amount of antioxidants/preservatives is generally preferred. Based on the invention all known antioxidants usually formulated into topical cosmetic or pharmaceutical compositions can be used. Especially preferred are antioxidants chosen from the group consisting of amino acids (e.g. glycine, histidine, tyrosine, tryptophan) and their derivatives, imidazole (e.g. urocanic acid) and derivatives, peptides such as D,L-carnosine, D-carnosine, L-carnosine and derivatives (e.g. anserine), carotenoids, carotenes (e.g. α-carotene, β-carotene, lycopene) and derivatives, chlorogenic acid and derivatives, lipoic acid and derivatives (e.g. dihydrolipoic acid), aurothioglucose, propylthiouracil and other thiols (e.g. thioredoxin, glutathione, cysteine, cystine, cystamine and its glycosyl-, N-acetyl-, methyl-, ethyl-, propyl-, amyl-, butyl- and lauryl-, palmitoyl-; oleyl-, γ-linoleyl-, cholesteryl- and glycerylester) and the salts thereof, dilaurylthiodipropionate, distearylthiodipropionate, thiodipropionic acid and its derivatives (ester, ether, peptides, lipids, nucleotides, nucleosides and salts) as well as sulfoximine compounds (such as buthioninsulfoximine, homocysteinesulfoximine, buthioninsulfone, penta-, hexa-, heptathioninsulfoximine) in very low compatible doses (e.g. pmol to μmol/kg), additionally (metal)-chelators (such as α-hydroxyfatty acids, palmic-, phytinic acid, lactoferrin), β-hydroxyacids (such as citric acid, lactic acid, malic acid), huminic acid, gallic acid, gallic extracts, bilirubin, biliverdin, EDTA, EGTA and its derivatives, unsaturated fatty acids and their derivatives (such as γ-linoleic acid, linolic acid, oleic acid), folic acid and its derivatives, ubiquinone and ubiquinol and their derivatives, vitamin C and derivatives (such as ascorbylpalmitate and ascorbyltetraisopalmitate, Mg-ascorbylphosphate, Na-ascorbylphosphate, Na-ascorbyl acetate), tocopherol and derivatives (such as vitamin-E-acetate), mixtures of nat. vitamin E, vitamin A and derivatives (vitamin-A-palmitate and -acetate) as well as coniferylbenzoate, rutinic acid and derivatives, α-glycosylrutin, ferulic acid, furfurylideneglucitol, carnosine, butylhydroxytoluene, butylhydroxyanisole, trihydroxybutyrophenone, urea and its derivatives, mannose and derivatives, zinc and derivatives (e.g. ZnO, ZnSO$_4$), selenium and derivatives (e.g. selenomethionin), stilbenes and derivatives (such as stilbenoxide, trans-stilbenoxide) and suitable derivatives (salts, esters, ethers, sugars, nucleotides, nucleosides, peptides and lipids) of the named active ingredients. One or more preservatives/antioxidants may be present in an amount about 0.01 wt. % to about 10 wt. % of the total weight of the topical cosmetic or pharmaceutical topical composition of the present invention. Preferably, one or more preservatives/antioxidants are present in an amount about 0.1 wt. % to about 1 wt. %.

Typically topical cosmetic or pharmaceutical compositions also contain surface active ingredients like emulsifiers, solubilizers and the like. An emulsifier enables two or more immiscible components to be combined homogeneously. Moreover, the emulsifier acts to stabilize the composition. Solubilizers that may be used in the present invention include but are not restricted to PEG/PPG-18/18 Dimethicone, PEG-40 Hydrogenated Castor Oil, PEG-20 Stearate, PEG-30 Glyceryl Stearate, and PEG-7 Glyceryl Cocoate. Emulsifiers that may be used in the present invention in order to form O/W, W/O, O/W/O or W/O/W emulsions/microemulsions include sorbitan oleate, sorbitan sesquioleate, sorbitan isostearate, sorbitan trioleate, polyglyceryl-3-diisostearate, polyglycerol esters of oleic/isostearic acid, polyglyceryl-6 hexaricinolate, polyglyceryl-4-oleate, polyglyceryl-4-oleate/ PEG-8 propylene glycol cocoate, oleamide DEA, TEA myristate, TEA stearate, magnesium stearate, sodium stearate, potassium laurate, potassium ricinoleate, sodium cocoate, sodium tallowate, potassium castorate, sodium oleate, and mixtures thereof. Furthermore, one or more synthetic polymers may be used as an emulsifier. For example, PVP eicosene copolymer, acrylates/$C_{10-30}$-alkyl acrylate crosspolymer, acrylates/steareth-20 methacrylate copolymer, PEG-22/dodecyl glycol copolymer, PEG-45/dodecyl glycol copolymer, and mixtures thereof. The preferred emulsifiers are PVP Eicosene copolymer, acrylates/$C_{10-30}$-alkyl acrylate crosspolymer, PEG-20 sorbitan isostearate, sorbitan isostearate, and mixtures thereof. The one or more emulsifiers are present in a total amount about 0.01 wt. % to about 20 wt. % of the total weight of the topical cosmetic or pharmaceutical topical composition of the present invention. Preferably, about 0.1 wt. % to about 10 wt. % of emulsifiers is used.

The lipid phase of the topical cosmetic or pharmaceutical compositions can advantageously be chosen from: mineral oils and mineral waxes; oils such as triglycerides of caprinic acid or caprylic acid and castor oil; oils or waxes and other natural or synthetic oils, in a preferred embodiment esters of fatty acids with alcohols e.g. isopropanol, propylene glycol, glycerin or esters of fatty alcohols with carboxylic acids or fatty acids; alkylbenzoates; and/or silicone oils such as dimethylpolysiloxane, diethylpolysiloxane, diphenylpolysiloxane, cyclomethicones and mixtures thereof.

Exemplary fatty substances which can be incorporated in the oil phase of the emulsion, microemulsion, oleo gel, hydrodispersion or lipodispersion of the topical cosmetic or pharmaceutical composition of the present invention are advantageously chosen from esters of saturated and/or unsaturated, linear or branched alkyl carboxylic acids with 3 to 30 carbon atoms, and saturated and/or unsaturated, linear and/or branched alcohols with 3 to 30 carbon atoms as well as esters of aromatic carboxylic acids and of saturated and/or unsaturated, linear or branched alcohols of 3-30 carbon atoms. Such esters can advantageously be selected from octylpalmitate, octylcocoate, octylisostearate, octyldodecylmyristate, cetearylisononanoate, isopropylmyristate, isopropylpalmitate, isopropylstearate, isopropyloleate, n-butylstearate, n-hexyllaureate, n-decyloleate, isooctylstearate, isononylstearate, isononylisononanoate, 2-ethyl hexyl palmitate, 2-ethylhexyllaurate, 2-hexyldecylstearate, 2-octyldodecyl palmitate, stearylheptanoate, oleyloleate, oleylerucate, erucyloleate, erucylerucate, tridecylstearate, tridecyltrimellitate, as well as synthetic, half-synthetic or natural mixtures of such esters e.g. jojoba oil.

Other fatty components suitable for use in the topical cosmetic or pharmaceutical compositions of the present invention include polar oils such as lecithins and fatty acid triglycerides, namely triglycerol esters of saturated and/or unsaturated, straight or branched carboxylic acid with 8 to 24 carbon atoms, preferably of 12 to 18 carbon-atoms whereas the fatty acid triglycerides are preferably chosen from synthetic, half synthetic or natural oils (e.g. cocoglyceride, olive oil, sun flower oil, soybean oil, peanut oil, rape seed oil, sweet almond oil, palm oil, coconut oil, castor oil, hydrogenated castor oil, wheat oil, grape seed oil, macadamia nut oil and others); apolar oils such as linear and/or branched hydrocarbons and waxes e.g. mineral oils, vaseline (petrolatum); paraffins, squalane and squalene, polyolefins, hydrogenated polyisobutenes and isohexadecanes, favored polyolefins are polydecenes; dialkyl ethers such as dicaprylylether; linear or cyclic silicone oils such as preferably cyclomethicones (octamethylcyclotetrasiloxane; cetyldimethicone, hexamethylcyclotrisiloxane, polydimethylsiloxane, poly(methylphenylsiloxane) and mixtures thereof.

Other fatty components which can advantageously be incorporated in topical cosmetic or pharmaceutical compositions of the present invention are isoeikosane; neopentylglycoldiheptanoate; propyleneglycoldicaprylate/dicaprate; caprylic/capric/diglycerylsuccinate; butyleneglycol caprylat/caprat; $C_{12-13}$-alkyllactate; di-$C_{12-13}$ alkyltartrate; triisostearin; dipentaerythrityl hexacaprylat/hexacaprate; propylene-glycolmonoisostearate; tricaprylin; dimethylisosorbid. Especially beneficial is the use of mixtures $C_{12-15}$-alkylbenzoate and 2-ethylhexylisostearate, mixtures $C_{12-15}$-alkylbenzoate and isotridecylisononanoate as well as mixtures of $C_{12-15}$-alkylbenzoate, 2-ethylhexylisostearate and isotridecylisononanoate.

The oily phase of the topical cosmetic or pharmaceutical compositions of the present invention can also contain natural vegetable or animal waxes such as bee wax, *china* wax, bumblebee wax and other waxes of insects as well as Shea butter and cocoa butter.

A moisturizing agent may be incorporated into a topical cosmetic or pharmaceutical composition of the present invention to maintain hydration or rehydrate the skin. Moisturizers that prevent water from evaporating from the skin by providing a protective coating are called emollients. Additionally an emollient provides a softening or soothing effect on the skin surface and is generally considered safe for topical use. Preferred emollients include mineral oils, lanolin, petrolatum, capric/caprylic triglyceraldehydes, cholesterol, silicones such as dimeticone, cyclometicone, almond oil, jojoba oil, avocado oil, castor oil, sesame oil, sunflower oil, coconut oil and grape seed oil, cocoa butter, olive oil aloe extracts, fatty acids such as oleic and stearic, fatty alcohols such as cetyl and hexadecyl (ENJAY), diisopropyl adipate, hydroxybenzoate esters, benzoic acid esters of $C_{9-15}$-alcohols, isononyl isononanoate, ethers such as polyoxypropylene butyl ethers and polyoxypropylene cetyl ethers, and $C_{12-15}$-alkyl benzoates, and mixtures thereof. The most preferred emollients are hydroxybenzoate esters, aloe vera, $C_{12-15}$-alkyl benzoates, and mixtures thereof. An emollient is present in an amount of about 1 wt. % to about 20 wt. % of the total weight of the topical cosmetic or pharmaceutical composition. The preferred amount of emollient is about 2 wt. % to about 15 wt. %, and most preferably about 4 wt. % to about 10 wt. %.

Moisturizers that bind water, thereby retaining it on the skin surface are called humectants. Suitable humectants can be incorporated into a topical cosmetic or pharmaceutical composition of the present invention such as glycerin, polypropylene glycol, polyethylene glycol, lactic acid, pyrrolidone carboxylic acid, urea, phospholipids, collagen, elastin, ceramides, lecithin sorbitol, PEG-4, and mixtures thereof. Additional suitable moisturizers are polymeric moisturizers of the family of water soluble and/or swellable/and/or with water gelating polysaccharides such as hyaluronic acid, chitosan and/or a fucose rich polysaccharide which is e.g. available as Fucogel®1000 (CAS-Nr. 178463-23-5) by SOLABIA S. One or more humectants are optionally present at about 0.5 wt. % to about 8 wt. % in a topical cosmetic or pharmaceutical composition of the present invention, preferably about 1 wt. % to about 5 wt. %.

The aqueous phase of the preferred topical cosmetic or pharmaceutical compositions of the present invention can contain the usual cosmetic or pharmaceutical additives such as alcohols, especially lower alcohols, preferably ethanol and/or isopropanol, low diols or polyols and their ethers, preferably propyleneglycol, glycerin, ethyleneglycol, ethyleneglycol monoethyl- or monobutylether, propyleneglycol monomethyl- or -monoethyl- or -monobutylether, diethyleneglycol monomethyl- or monoethylether and analogue products, polymers, foam stabilizers; electrolytes and especially one or more thickeners. However, preferably the topical cosmetic or pharmaceutical compositions of the present invention are free of ethanol, more preferably they are free of alcohols, and most preferably they are free of organic solvents, since such compounds can cause skin irritation.

Thickeners that may be used in topical cosmetic or pharmaceutical compositions of the present invention to assist in making the consistency of a product suitable include carbomer, siliciumdioxide, magnesium and/or aluminium silicates, beeswax, stearic acid, stearyl alcohol polysaccharides and their derivatives such as xanthan gum, hydroxypropyl cellulose, polyacrylamides, acrylate crosspolymers preferably a carbomer, such as Carbopole® of type 980, 981, 1382, 2984, 5984 alone or mixtures thereof.

Suitable neutralizing agents which may be included in the topical cosmetic or pharmaceutical composition of the present invention to neutralize components such as e.g. an emulsifier or a foam builder/stabilizer include but are not limited to alkali hydroxides such as a sodium and potassium hydroxide; organic bases such as diethanolamine (DEA), triethanolamine (TEA), aminomethyl propanol, and mixtures thereof; amino acids such as arginine and lysine and any combination of any foregoing. The neutralizing agent can be present in an amount of about 0.01 wt. % to about 8 wt. % in the topical cosmetic or pharmaceutical composition of the present invention, preferably, 1 wt. % to about 5 wt. %.

The addition of electrolytes into the topical cosmetic or pharmaceutical composition of the present invention may be necessary to change the behavior of a hydrophobic emulsifier. Thus, the emulsions/microemulsions of this invention may contain preferably electrolytes of one or several salts including anions such as chloride, sulfates, carbonate, borate and aluminate, without being limited thereto. Other suitable electrolytes can be on the basis of organic anions such as, but not limited to, lactate, acetate, benzoate, propionate, tartrate and citrate. As cations preferably ammonium, alkylammonium, alkali- or alkaline earth metals, magnesium-, iron- or zinc-ions are selected. Especially preferred salts are potassium and sodium chloride, magnesium sulfate, zinc sulfate and mixtures thereof. Electrolytes can be present in an amount of about 0.01 wt. % to about 8 wt. % in the topical cosmetic or pharmaceutical composition of the present invention.

The topical cosmetic or pharmaceutical compositions of the present invention is preferably applied at least once per day, e.g. twice or triple times a day.

The composition according to the invention can also contain one or more additional pharmaceutically or cosmetically active ingredient, in particular for skin lightening, tanning prevention, treatment of hyperpigmentation, preventing or reducing acne, wrinkles, lines, atrophy, inflammation, as well as topical anesthetics, antimicrobial agents, and antifungal agents, chelators and sequestrants; anti-cellulites agents and sunscreening additives. Examples of such ingredients are peptides (e.g., Matrixyl™, Syn®-Coll), oligopeptides, wax-based synthetic peptides (e.g., octyl palmitate and tribehenin and sorbitan isostearate and palmitoyl-oligopeptide), glycerol, urea, guanidine (e.g. amino guanidine); vitamins and derivatives thereof such as vitamin C (ascorbic acid), vitamin A (e.g., retinoid derivatives such as retinyl palmitate or retinyl propionate), vitamin E (e.g., tocopherol acetate), vitamin $B_3$ (e.g. niacinamide) and vitamin $B_5$ (e.g. panthenol), vitamin $B_6$ and vitamin $B_{12}$, biotin, folic acid; anti-acne actives or medicaments (e.g. resorcinol, salicylic acid, and the like); antioxidants (e.g. phytosterols, lipoic acid); flavonoids (e.g. isoflavones, phytoestrogens); skin soothing and healing agents such as aloe vera extract, allantoin and the like; agents suitable for aesthetic purposes such as essential oils, fragrances, skin sensates, opacifiers, aromatic compounds (e.g., clove oil, menthol, camphor, eucalyptus oil, and eugenol), desquamatory actives, hydroxy acids such as AHA acids, radical scavengers, farnesol, antifungal actives in particular bisabolol, alkyldiols such as 1,2-pentanediol, hexanediol or 1,2-octanediol, phytol, polyols such as phytanetriol, ceramides and pseudoceramides, amino acids, protein hydrolysates, polyunsaturated fatty acids, plant extracts like kinetin, DNA or RNA and their fragmentation products, carbohydrates, conjugated fatty acids, carnitin, carnosine, biochinonen, phytofluen, phytoen, and their corresponding derivatives.

It is also an object of the present invention to provide the use of a compound of formula (1) with the definitions and preferences regarding the compound of formula (1), and composition as given above for tanning prevention of human skin, smoothening of human skin color irregularities, skin lightening/brightening, and/or reducing melanin production in human skin.

Most preferably, the present invention provides the use of a topical composition comprising danielone, or a methyl, ethyl or propyl ester of danielone or any mixture thereof for tanning prevention of human skin, smoothening of human skin color irregularities, skin lightening/brightening, and/or reducing melanin production in human skin.

Additionally, it is also an object of the present invention to provide a compound of formula (1) with the definitions and preferences regarding the compound of formula (1), and composition as given above, for use in a topical pharmaceutical composition for the treatment and prevention of skin pigmentation disorders. Skin pigmentation disorders include (i) primary hyper-pigmentation disorders which include those that are nevoid, congenital or acquired such as local hyperpigmented disorders which include pigmented nevi, ephelides (juvenile freckles, an inherited characteristic; age spots; and café-au-lait spots) and lentigines (solar lentigines, senile lentigines, senile freckles, liver-spots); and (ii) secondary hyperpigmentation disorders which include those occurring after a separate dermatologic condition, including acne; such disorders are most commonly seen in dark-skinned individuals and are called post-inflammatory hyper-pigmentation.

Further hyper-pigmentation disorders which include arsenical melanosis and disorders associated with Addison's disease; freckling and café-au-lait spots produced by neurofibromatosis; regional or patterned hyperpigmentation caused by melanocytic hyperactivity, such as idiopathic melasma occurring either during pregnancy or secondary to estrogen-progesterone contraception.

Other examples for disorders which, in accordance with the invention, may be treated or prevented by topical application of a compound of formula (1) according to the present invention include the pigmentation following physical trauma, eczematoid eruptions are lupus erythematosus, and dermatoses such as *pityriasis rosea*, psoriasis, dermatitis herpetiformis, fixed drug eruptions, photodermatitis and Lichen simplex chronicus, *tinea versicolor* (under specific environmental conditions for a yeast type of skin fungus, present on normal skin) and *Acanthosis nigricans*; post-inflammatory hyperpigmentations which can result due to abrasion, burns, wounds, insect bites, dermatitis, and other similar small, fixed pigmented lesions; Berloque hyperpigmentation, which is due to phototoxicity from chemicals in the rinds of limes and other citrus fruits, and to celery; and accidental hyperpigmentation which can result from post-lesional photosensitization and scarring.

Further examples of pigmentation disorders include those caused by some drugs, including chloroquine, chlorpromazine, minocycline and amiodarone. Benzoyl peroxide, fluorouracil and tretinoin can cause hyperpigmentation; fixed drug eruptions can result from phenolphthalein in laxatives, trimethoprim-sulfamethoxazole, nonsteroidal anti-inflammatory drugs (NSAIDs) and tetracyclines.

In certain forms of leukoderma such as vitiligo where, if the injured skin cannot be repigmented, the residual zone of normal skin are depigmented to impart a homogeneous white colour to the entire skin. In all these conditions treatment in accordance with the invention may be considered.

The present invention also relates to a method of lightening human skin which comprises topically administering an effective amount of a compound of formula (1) or (2)

formula (1):

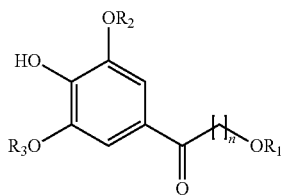

wherein, n is an integer comprised between 1 and 5, $R_1$ is H or an aliphatic straight or branched carbon chain of 1 to 5 carbon atoms $R_2$ and $R_3$ are both independently an aliphatic straight or branched carbon chain of 1 to 6 carbon atoms to the appropriate skin area of a person in need of such cosmetic benefit.

Furthermore, it also relates to a method of treating or preventing pigmentation disorders which comprises topically administering an effective amount of a compound of formula (1)

formula (1):

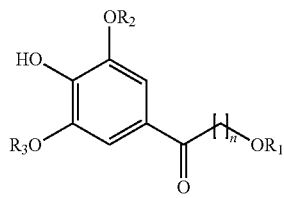

wherein, n is an integer comprised between 1 and 5, $R_1$ is H or an aliphatic straight or branched carbon chain of 1 to 5 carbon atoms $R_2$ and $R_3$ are both independently an aliphatic straight or branched carbon chain of 1 to 6 carbon atoms to the appropriate skin area of a person in need of such treatment.

The term 'an effective amount' refers to an amount necessary to obtain a physiological effect. The physiological effect may be achieved by one application dose or by repeated applications. The dosage administered may, of course, vary depending upon known factors, such as the physiological characteristics of the particular composition comprising the fatty acid or a salt, ester or amide with the definitions and preferences as given above, optionally in combination with a retinoid and its mode and route of administration; the age, health and weight of the recipient; the nature and extent of the symptoms; the kind of concurrent treatment; the frequency of treatment; and the effect desired and can be adjusted by a person skilled in the art.

The present invention also relates to a method as described above, wherein, from about 0.2 µg to about 200 µg of compound of formula (1) are applied per square centimeter of skin per day.

The present invention also relates to a method as described above, wherein at least one additional skin lightening agent and/or UV screening agent is additionally administered.

The usefulness of skin lightening agent for tanning prevention, to lightening natural skin color or to brighten hyperpigmented skin areas can be determined by methods known in the art, see, e.g., Greatens, A., et al., Effective inhibition of melanosome transfer to keratinocytes by lectins and niacinamide is reversible. Experimental Dermatology, 2005. 14(7): p. 498-508; Hakozaki, T., et al., *The effect of niacinamide on reducing cutaneous pigmentation and suppression of melanosome transfer*. British journal of dermatology FIELD Publication Date: 2002 July, 2002. 147(1): p. 20-31; Griffiths, C. E., et al., *Topical tretinoin (retinoic acid) improves melasma. A vehicle-controlled, clinical trial*. British journal of dermatology FIELD Publication Date: 1993 October, 1993. 129(4): p. 415-21; and Hayakawa, R., et al., *Biochemical and clinical study of calcium pantetheine-S-sulfonate*. Acta vitaminologica et enzymologica FIELD Publication Date: 1985, 1985. 7(1-2): p. 109-14.

Following the clinical study design as especially mentioned at Greatens et al, supra, and Hakozaki et al., supra, an O/W skin lightening cream such as mentioned in Example 3 including the ingredient to be tested at different concentrations ranging from 0.1% to 10% or even more preferable from 1% to 5% is done. Briefly, a human clinical study is performed in a double-blinded, randomized, vehicle-controlled, split-face design with at least 30 people per group. Application is done in a dosage-controlled manner twice daily over at least 4 weeks, more preferable over 8 weeks and especially over 12 weeks. Quantification of lightening effects can be performed with several methods such as self-assessment Hakozaki et al., supra, visual assessment Greatens et al., supra, assessment by image analysis or assessment by a chromameter (Hakozaki et al., supra). Briefly, to identify a valid skin lightening agent a self-assessment should result that more than 50% of a treatment group realized at least a slightly brightening. For the visual assessment a reviewers' evaluation of at least 8 people is done with a grading from 1 to 4 and should result in a significant difference of the means with a p-value <0.05. An assessment by image analysis is done by using CCD camera system and quantifying basal skin color (L*, a*, b*) and area of hyperpigmentation ($mm^2$) by computer analysis of the video images. Basal skin color can be quantified either as delta L*a*b* or as ITA° depending on L* and b* for brown pigmentation only. Data are only valid with a p-value <0.05. Assessment by a chromameter is done in the same way as described for image analysis using L*a*b*- and/or ITA°-values for quantification.

The following Examples are illustrative but not limitative of the invention.

EXAMPLES

Example 1

Effect of Danielone in Melanocyte Cell Culture

Test Compounds
Compounds were prepared at concentrations of 1% in DMSO as solvent.
Assays
Cytotoxicity:
Cytotoxicity was measured using the MTT assay (Roche). In brief: Normal human melanocytes moderately pigmented (HEMn-MP) were precultured for 24 hrs, and then incubated with compounds for three days. We then added MTT (Roche) labeling reagent 10 µl to each well (final concentration 0.5 mg/ml) and incubated the microtiterplate for 4 hrs at 37° C., and under 5% $CO_2$. After addition of 100 µl solubilisation solution into each well, the plate was allowed to stand overnight in the incubator (37° C., 5% $CO_2$. The absorbance OD 550 nm was measured in an absorbance plate reader (ELX 800 BIO-TEK Instrument) and the data is shown in Table 1.

TABLE 1 results of the cytotoxicity assay at different danielone concentrations

| Compound: | Concentration [%]: | Viability [%]: | Standard deviation [%]: |
|---|---|---|---|
| Danialone | 0 | 100 | 5 |
| | 0.025 | 51 | 1 |
| | 0.0025 | 113 | 1 |
| | 0.00025 | 112 | 5 |

Quantification of Melanin Synthesis in Cell Culture:
Normal human melanocytes moderately pigmented (HEMn-MP) were seeded in 96 well cell culture plates (20'000 cells per well) and grown to sub-confluence for three days in a 1:2 mixture of M2-Medium (Clonetics) and Promocell-Medium together 'Culture medium'. Culture medium was exchanged with Culture Medium containing compound and melanogenesis progressed for another three days in an incubator at a temperature of 37° C. and at 5% $CO_2$ atmosphere. Including cell layer and culture supernatant total melanin was extracted using 1.7M KOH with shaking at 300 rpm for approximately 1 hour at room temperature. We measured melanin content at 405 nm in an absorbance plate reader. The experiment was done at least in triplicates and the average of triplicates is shown in Table 2. We use phenylthiourea (PTU) as a positive control at a concentration of 0.0152% (1 mM). PTU is a tyrosinase inhibitor (Poma 1999) and is commonly used as a reference in cell pigmentation assays (see e.g. Le Pape 2008).

TABLE 2

Quantification of melanin in cell culture

| Compound: | Concentration [%]: | Total melanin [%]: | Standard deviation [%] |
|---|---|---|---|
| Baseline | | 100 | 3 |
| PTU | 0.0152 | 58 | 5 |
| Danielone | 0.0025 | 66 | 16 |
| | 0.00125 | 75 | 7 |
| | 0.000625 | 104 | 7 |

Cell-Pellet Depigmentation Assay:
Human melanocytes moderately pigmented (HEMn-MP) were seeded in 6-well culture plates at a cell density of 2×10E5 cells/mL and preincubated for three days in a 1:2 mixture of M2-Medium (Clonetics) and Promocell-Medium together 'Culture medium' in an incubator at a temperature of 37° C. and at 5% $CO_2$ Atmosphere. Culture medium was exchanged with Culture Medium containing compound and melanogenesis progressed for another three days in an incubator at same incubation conditions as described above. Compound dilutions were done in duplicates. Cells were harvested after trypsinization and pooled in eppendorf-tubes, centrifugated and supernatant removed. The remaining cell pellet was photographed and visually checked for whitening effects. The pellets were scored for their darkness in a scale 1 to 5 (5 corresponding to dark control cell pellet) and 1 corresponding to a very light brown cell pellet. Results are summarized in Table 3.

TABLE 3

Results of the cell depigmenting effect:

| Compound | Darkness level of the cell pellet |
|---|---|
| Control | 5 |
| PTU 0.0152% | 1 |
| Danielone 0.0025% | 2 |

Example 2

Skin Lightening Cream (O/W)

This example and the following examples are concerned with topical compositions which may be prepared by procedures known per se in the art.

| Ingredients | % (w/w) |
|---|---|
| Estol 3650 (Glyceryl Myristate) | 5.00 |
| Lanette 16 (Cetyl Alcohol) | 2.00 |
| Tegosoft M (Isopropyl Myristate) | 10.00 |
| Vitamin E Acetate (Tocopheryl Acetate) | 0.50 |
| Almond Oil | 2.00 |
| BHT | 0.05 |
| Phenonip (Phenoxyethanol & Methylparaben & Ethylparaben & Propylparaben & Butylparaben & | 0.60 |

-continued

| Ingredients | % (w/w) |
|---|---|
| Isopropylparaben) | |
| Tris (Tromethamine) | 0.90 |
| EDETA BD (Disodium EDTA) | 0.10 |
| Propylene Glycol | 5.00 |
| Danielone | 0.01 |
| Sepigel 305 (Polyacrylamide & C13-14 Isoparaffin & Laureth-7) | 2.00 |
| Triethanolamine | q.s. |
| Water deionized | ad 100 |

Example 3

Skin Lightening Cream (O/W)

| Ingredients | % (w/w) |
|---|---|
| Estol 3650 (Glyceryl Myristate) | 5.00 |
| Lanette 16 (Cetyl Alcohol) | 2.00 |
| Brij 72 (Steareth-2) | 2.00 |
| Brij 721 (Steareth-21) | 2.00 |
| Tegosoft M (Isopropyl Myristate) | 10.00 |
| Bisabolol | 0.20 |
| Vitamine E Acetate (Tocopheryl Acetate) | 1.00 |
| Almond Oil | 2.00 |
| BHT | 0.05 |
| Phenonip (Phenoxyethanol & Methylparaben & Ethylparaben & Propylparaben & Butylparaben & Isopropylparaben) | 0.60 |
| EDETA BD (Disodium EDTA) | 0.10 |
| Propylene Glycol | 10.00 |
| Sodium Ascorbyl Phosphate | 0.1 |
| Arbutin | 1.00 |
| D-Panthenol | 0.50 |
| Niacinamide | 0.20 |
| Salicylic acid | 0.50 |
| Danielone | 0.01 |
| Sepigel 305 (Polyacrylamide & C13-14 Isoparaffin & Laureth-7) | 2.00 |
| Triethanolamine | q.s. |
| Water deionized | ad 100 |

Example 4

Skin Lightening Cream with UV Protection (Indicative SPF: 8, O/W)

| Ingredients | % (w/w) |
|---|---|
| Estol 3650 (Glyceryl Myristate) | 5.00 |
| Lanette 16 (Cetyl Alcohol) | 2.00 |
| Brij 72 (steareth-2) | 2.00 |
| Brij 721 (steareth-21) | 2.00 |
| Tegosoft M (Isopropyl Myristate) | 10.00 |
| BHT | 0.05 |
| Ascorbyl Palmitate | 0.50 |
| Parsol 1789 (Butyl Methoxydibenzoylmethane) | 1.00 |
| Parsol MCX (Ethyl Hexylmethoxycinnamate) | 2.00 |
| Eusolex OS (Octyl Salicylate) | 2.00 |
| Phenonip (Phenoxyethanol & Methylparaben & Ethylparaben & Propylparaben & Butylparaben & Isopropylparaben) | 0.60 |
| EDETA BD (Disodium EDETA) | 0.10 |
| Danielone | 0.5 |
| Propyleneglycol | 8.00 |
| Sepigel | 2.00 |
| Triethanolamine | q.s. |
| Water deionized | ad 100 |

Example 5

Skin Lightening Cream (W/O)

| Ingredients | % (w/w) |
|---|---|
| Cremophor WO7 (PEG-7 Hydrogenated Castor Oil) | 6.00 |
| Elfacos ST 9 (PEG-45/Dodecyl Glycol Copolymer) | 2.00 |
| Myritol 318 (Caprylic/Capric Triglyceride) | 5.00 |
| Lunacera M (Micro wax) | 2.00 |
| Paraffin Oil | 10.00 |
| Danielone | 0.1 |
| Phytantriol | 0.10 |
| Vitamine E Acetate (Tocopheryl Acetate) | 1.00 |
| Jojoba Oil | 5.00 |
| BHT | 0.05 |
| Phenonip (Phenoxyethanol & Methylparaben & Ethylparaben & Propylparaben & Butylparaben & Isopropylparaben) | 0.60 |
| EDETA BD (Disodium EDTA) | 0.10 |
| D-Panthenol | 0.50 |
| Propylene Glycol | 5.00 |
| Kojic Acid | 1.00 |
| Water deionized | Ad 100 |

Example 6

Skin Lightening Gel

| Ingredients | % (w/w) |
|---|---|
| Pemulen TR-1 (Acrylate/C10-30 Alkyl Acrylate Crosspolymer) | 0.80 |
| Biotin | 0.01 |
| EDETA BD (Disodium EDTA) | 0.10 |
| D-Panthenol | 0.20 |
| Hyasol BT (Sodium Hyaluronate) | 1.00 |
| Euxyl K 400 (Methyldibromo Glutaronitrile & Phenoxyethanol) | 0.20 |
| NaOH (30%) | 1.00 |
| Propylene Glycol | 5.00 |
| Epigallocatechin Gallate | 0.50 |
| Genistein | 0.10 |
| Niacinamide | 0.50 |
| Emblica (*Phyllanthus Emblica* fruit extract) | 0.50 |
| Hydroquinone | 0.20 |
| Danielone | 0.005 |
| Citric Acid (10%) | q.s. |
| Water deionized | ad 100 |

Example 7

Skin Lightening Lotion

| Ingredients | % (w/w) |
|---|---|
| Propylene Glycol | 5.00 |
| Danielone | 0.005 |
| D-Panthenol | 0.50 |
| Sodium PCA | 0.25 |
| Ethanol | 10.00 |
| Citric Acid (10%) | q.s. |
| Water deionized | Ad 100 |

Example 8

Skin Lightening Cream with UV Protection
(Indicative SPF: 8, O/W)

| Ingredients | % (w/w) |
| --- | --- |
| PARSOL SLX (Dimethico Diethylbenzalmalonate) | 8.00 |
| Uvinul Titanium Dioxide (Titanium Dioxide) | 2.00 |
| Tegosoft TN (C12-15 Alkyl Benzoate) | 5.00 |
| Silicone 2503 Cosmetic Wax (Stearyl Dimethicone) | 2.00 |
| Cetyl Alcohol | 1.00 |
| Butylated Hydroxytoluene (BHT) | 0.05 |
| Estol GMM 3650 (Glyceryl Myristate) | 4.00 |
| Edeta BD (Disodium EDTA) | 0.10 |
| Phenonip (Phenoxyethanol & Methylparaben & Ethylparaben & Propylparaben & Butylparaben) | 0.60 |
| Carbopol 980 (Carbomer) | 10.00 |
| Danielone | 0.002 |
| Propylene Glycol | 5.00 |
| KOH sol. 10% | 0.50 |
| Water deionized | ad 100 |

Example 9

Skin Lightening Gel

| Ingredients | % (w/w) |
| --- | --- |
| Pemulen TR-1 (Acrylate/C10-30 Alkyl Acrylate Crosspolymer) | 0.80 |
| EDETA BD (Disodium EDTA) | 0.10 |
| D-Panthenol | 0.10 |
| Hyasol BT (Sodium Hyaluronate) | 1.00 |
| Euxyl K 400 (Methyldibromo Glutaronitrile & Phenoxyethanol) | 0.20 |
| NaOH (30%) | 1.00 |
| Propylene Glycol | 5.00 |
| Melawhite (Water and Leucocyte extract) | 1.00 |
| Kojic Acid | 0.10 |
| Niacinamide | 0.10 |
| Danielone | 0.002 |
| Citric Acid (10%) | q.s. |
| Water deionized | Ad 100 |

Example 10

Skin Lightening Gel

| Ingredients | % (w/w) |
| --- | --- |
| Pemulen TR-1 (Acrylate/C10-30 Alkyl Acrylate Crosspolymer) | 0.80 |
| Biotin | 0.01 |
| EDETA BD (Disodium EDTA) | 0.10 |
| D-Panthenol | 0.10 |
| Hyasol BT (Sodium Hyaluronate) | 1.00 |
| Euxyl K 400 (Methyldibromo Glutaronitrile & Phenoxyethanol) | 0.20 |
| NaOH (30%) | 1.00 |
| Propylene Glycol | 5.00 |
| Melfade (Water and Glycerin and Bearberry extract) | 1.00 |
| Kojic Acid | 0.10 |
| Danielone | 0.01 |
| Citric Acid (10%) | q.s. |
| Water deionized | Ad 100 |

Example 11

Skin Lightening Gel

| Ingredients | % (w/w) |
| --- | --- |
| Pemulen TR-1 (Acrylate/C10-30 Alkyl Acrylate Crosspolymer) | 0.80 |
| EDETA BD (Disodium EDTA) | 0.10 |
| D-Panthenol | 0.10 |
| Hyasol BT (Sodium Hyaluronate) | 1.00 |
| Euxyl K 400 (Methyldibromo Glutaronitrile & Phenoxyethanol) | 0.20 |
| NaOH (30%) | 1.00 |
| Propylene Glycol | 10.00 |
| Licorice extract | 0.50 |
| Mulberry extract | 0.50 |
| Kojic Acid | 0.50 |
| Niacinamide | 0.50 |
| Danielone | 0.05 |
| Citric Acid (10%) | q.s. |
| Water deionized | ad 100 |

Example 12

Skin Lightening Gel

| Ingredients | % (w/w) |
| --- | --- |
| Carbopol ETD 2020 (Carbomer) | 0.80 |
| Panthenol | 0.50 |
| Niacinamide | 0.10 |
| NaOH (30%) | 0.50 |
| Ethanol | 35.00 |
| Propylene Glycol | 8.00 |
| Danielone | 0.01 |
| Water deionized | ad 100 |

Example 13

Skin Lightening Cream with UV Protection
(Indicative SPF: 8, O/W)

| Ingredients | % w/w |
| --- | --- |
| Parsol 1789 (Butyl Methoxydibenzoylmethane) | 1.50 |
| Uvinul Titanium Dioxide (Titanium Dioxide) | 3.00 |
| Parsol MCX (Ethyl Hexylmethoxycinnamate) | 4.00 |
| Tegosoft TN (C12-15 Alkyl Benzoate) | 8.00 |
| Silicone 2503 Cosmetic Wax (Stearyl Dimethicone) | 2.00 |
| Cetyl Alcohol | 1.00 |
| Butylated Hydroxytoluene (BHT) | 0.05 |
| Estol GMM 3650 (Glyceryl Myristate) | 4.00 |
| Edeta BD (Disodium EDTA) | 0.10 |
| Phenonip (Phenoxyethanol & Methylparaben & Ethylparaben & Propylparaben & Butylparaben) | 0.60 |
| Carbopol 980 (Carbomer) | 10.00 |
| Danielone | 0.01 |
| Propylene Glycol | 5.00 |
| KOH sol. 10% | 0.50 |
| Water deionized | ad 100 |

Example 14

Skin Lightening Cream with UV Protection
(Indicative SPF: 10, O/W)

| Ingredients | % w/w |
|---|---|
| PARSOL SLX (Polysilicone 15) | 6.00 |
| PARSOL 1789 (Butyl Methoxydibenzoylmethane) | 2.00 |
| Parsol MCX (Ethyl Hexylmethoxycinnamate) | 4.00 |
| Softisan 100 (Hydrogenated Coco-Glycerides) | 2.00 |
| Glyceryl Myristate | 4.00 |
| Myritol 318 (Caprylic/Capric Triglyceride) | 7.00 |
| Cosmacol ESI (Tridecyl Salicylate) | 8.00 |
| VITAMIN E ACETATE (Tocopheryl Acetate) | 0.50 |
| Phenonip (Phenoxyethanol & Methylparaben & Ethylparaben & Propylparaben & Butylparaben | 0.80 |
| 1,2-Propylene Glycol (Propylene Glycol) | 5.00 |
| Carbopol ETD 2020 (Acrylate/C10-30 Alkyl Acrylate Crosspolymer) | 0.30 |
| Edeta BD (Disodium EDTA) | 0.10 |
| KOH 10% sol.(Potassium Hydroxide) | 1.60 |
| STAY-C 50 (Sodium Ascorbyl Phosphate) | 0.1 |
| Danielone | 0.01 |
| Retinyl Palmitate | 0.50 |
| VITAMIN E (Tocopherol) | 0.10 |
| Water deionized | ad 100 |

Example 15

Skin Lightening Liquid Soap

| Ingredients | % w/w |
|---|---|
| Texapon NSO (Sodium Laureth Sulfate) | 40.00 |
| Tego Betain L7 (Cocamidopropyl Betaine) | 10.00 |
| Lamepon S (Potassium Cocoyl Hydrolysed Collagen) | 5.00 |
| Plantaren 1200 (Lauryl Glucoside) | 5.00 |
| Cetiol HE (PEG-7 Glyceryl Cocoate) | 3.00 |
| Preservative | q.s. |
| Polymer JR 400 (Polyquaternium-10) | 0.20 |
| Panthenol 75 L (Panthenol) | 0.40 |
| Danielone | 0.005 |
| EDETA BD (Disodium EDTA) | 0.10 |
| Vitamine E Acetate (Tocopheryl Acetate) | 0.30 |
| Cremophor RH 40 (PEG-40 Hydrogenated Castor Oil) | 2.00 |
| Sodium Chloride | 1.00 |
| Water deionized | ad 100 |

Example 16

Effect on Melanogenesis: Comparative Example ?

Quantification of Melanin Synthesis in Cell Culture:

Normal human melanocytes NHM (HEMn-MP) were seeded in 96 well cell culture plates (20'000 cells per well) and grown to sub-confluence for three days in a 1:2 mixture of M2-Medium (Clonetics) and Promocell-Medium together 'Culture medium'. Culture medium was exchanged with Culture Medium containing compound and melanogenesis progressed for another three days at a temperature of 37° C. and at 5% $CO_2$ atmosphere. Including cell layer and culture supernatant total melanin was extracted using 1.7M KOH with shaking at 300 rpm for approximately 1 hour at RT. We measured melanin content at 405 nm in an absorbance plate reader. The experiment was done in triplicates. We used PTU as a positive control.

The skin whitening activity of danielone: (compound of formula (I) with n=1, $R_1$, $R_2$, and $R_3$=methyl) has been compared to: beta-hydroxypropiovanillon (equivalent to compound of formula (I) wherein n=2, $R_1$, and $R_2$, =methyl, wherein $OR_3$ has been replaced by H.

The table below shows that at all three concentrations tested, danielone is very efficient, wherein the compound wherein OR3 is replaced by H has no activity.

| Compound | Concentration | % melanin inhibition | STD |
|---|---|---|---|
| Danielone | 0.01% | −49.25 | 8.30 |
|  | 0.005% | −40.20 | 10.70 |
|  | 0.0025% | 1.51 | 7.44 |
| beta-hydroxypropiovanillon | 0.01% | 4.26 | 11.26 |
|  | 0.005% | 7.45 | 17.58 |
|  | 0.0025% | 7.45 | 6.98 |

What is claimed is:

1. A method of lightening human skin which comprises topically administering an effective amount of a compound of formula (1)
formula (1):

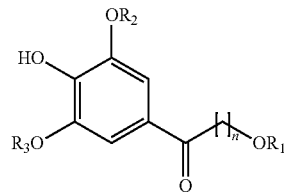

wherein,
n is an integer comprised between 1 and 5,
$R_1$ is H or an aliphatic straight or branched carbon chain of 1 to 5 carbon atoms,
$R_2$ and $R_3$ are both independently an aliphatic straight or branched carbon chain of 1 to 6 carbon atoms
to the appropriate skin area of a person in need of such cosmetic benefit.

2. A method of treating pigmentation disorders which comprises topically administering an effective amount of a compound of formula (1)
formula (1):

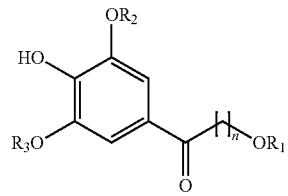

wherein,
n is an integer comprised between 1 and 5,
$R_1$ is H or an aliphatic straight or branched carbon chain of 1 to 5 carbon atoms,
$R_2$ and $R_3$ are both independently an aliphatic straight or branched carbon chain of 1 to 6 carbon atoms
to the appropriate skin area of a person in need of such treatment.

3. The method as in claim 2 wherein from about 0.2 µg to about 200 µg of compound of formula (1) or (2) are applied per square centimeter of skin per day.

4. The method as in claim 2 wherein at least one additional skin lightening agent and/or UV screening agent is additionally administered.

\* \* \* \* \*